(12) United States Patent
Nason et al.

(10) Patent No.: US 11,553,907 B2
(45) Date of Patent: *Jan. 17, 2023

(54) SYSTEMS AND METHODS FOR REPAIRING SOFT TISSUES

(71) Applicant: CAYENNE MEDICAL, INC., Scottsdale, AZ (US)

(72) Inventors: Kevin S. Nason, Chandler, AZ (US); Kevin N. Baird, Scottsdale, AZ (US); Derek J. Harper, Scottsdale, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 716 days.

This patent is subject to a terminal disclaimer.

(21) Appl. No.: 16/560,578

(22) Filed: Sep. 4, 2019

(65) Prior Publication Data
US 2020/0022695 A1  Jan. 23, 2020

Related U.S. Application Data

(63) Continuation of application No. 15/161,234, filed on May 21, 2016, now Pat. No. 10,499,901.
(Continued)

(51) Int. Cl.
*A61B 17/04* (2006.01)
*A61B 17/00* (2006.01)

(52) U.S. Cl.
CPC .......... *A61B 17/0401* (2013.01); *A61B 2017/00336* (2013.01); *A61B 2017/00831* (2013.01);
(Continued)

(58) Field of Classification Search
CPC ...... A61B 17/0401; A61B 2017/00336; A61B 2017/0403; A61B 2017/0406; A61F 2/0811
See application file for complete search history.

(56) References Cited

U.S. PATENT DOCUMENTS 5,578,057 A  11/1996  Wenstrom, Jr.
6,123,711 A   9/2000  Winters
(Continued)

FOREIGN PATENT DOCUMENTS

CN  107847253 A   3/2018
JP  2007533371 A  11/2007
(Continued)

OTHER PUBLICATIONS

"U.S. Appl. No. 15/161,234, Corrected Notice of Allowability dated Oct. 30, 2019", 2 pgs.
(Continued)

*Primary Examiner* — John P Lacyk
(74) *Attorney, Agent, or Firm* — Schwegman Lundberg & Woessner, P.A.

(57) ABSTRACT

A wicking component is integrated into an arthroscopically deployable bone anchor, and is intended to improve soft tissue-to-bone repair. Once deployed, the fibrous wick component extends from within the bone tunnel, out of the hole, and to the bone-tendon interface on the bone surface. The tissue is approximated against the bone, sandwiching the wick material between the bone and tissue. The wick component is ideally a polymeric fibrous or tissue-based scaffold that provides a pathway for cells (autologous bone marrow constituents and blood) to travel from within the bone to the soft tissue-bone interface, accelerating and promoting the healing response. The system provides a biomimetic structure that stimulates the extracellular matrix to encourage cell attachment and potentially improve the healing response. The wick component does not need to be integrated into a suture anchor and installed when the suture anchor is deployed. For example, the wick component could be placed above or near a traditional suture anchor after it has been deployed.

20 Claims, 9 Drawing Sheets

Related U.S. Application Data

(60) Provisional application No. 62/165,822, filed on May 22, 2015.

(52) U.S. Cl.
CPC .............. *A61B 2017/00884* (2013.01); *A61B 2017/0403* (2013.01); *A61B 2017/0409* (2013.01); *A61B 2017/0412* (2013.01); *A61B 2017/0427* (2013.01)

(56) References Cited

U.S. PATENT DOCUMENTS

| | | | |
|---|---|---|---|
| 7,704,271 | B2 | 4/2010 | Abdou |
| 8,080,060 | B2 | 12/2011 | Govil et al. |
| 8,795,334 | B2 | 8/2014 | Astorino et al. |
| 8,986,327 | B2 | 3/2015 | Karasic et al. |
| 9,173,645 | B2 | 11/2015 | Overes et al. |
| 9,320,512 | B2 | 4/2016 | Dooney, Jr. |
| 9,700,291 | B2 | 7/2017 | Norton et al. |
| 9,901,334 | B2 | 2/2018 | Baird et al. |
| 10,499,901 | B2 * | 12/2019 | Nason ................ A61B 17/0401 |
| 10,631,849 | B2 | 4/2020 | Baird et al. |
| 2006/0149266 | A1 | 7/2006 | Cordasco |
| 2007/0010857 | A1 | 1/2007 | Sugimoto et al. |
| 2007/0255317 | A1 | 11/2007 | Fanton et al. |
| 2008/0154314 | A1 | 6/2008 | Mcdevitt |
| 2008/0188936 | A1 | 8/2008 | Ball et al. |
| 2008/0281325 | A1 | 11/2008 | Stone et al. |
| 2009/0062850 | A1 | 3/2009 | Ken |
| 2009/0306776 | A1 | 12/2009 | Murray |
| 2009/0317446 | A1 | 12/2009 | Tan et al. |
| 2010/0047309 | A1 | 2/2010 | Lu et al. |
| 2011/0028997 | A1 | 2/2011 | Gregoire et al. |
| 2011/0098727 | A1 | 4/2011 | Kaiser et al. |
| 2011/0264140 | A1 | 10/2011 | Lizardi et al. |
| 2011/0288566 | A1 | 11/2011 | Kubiak |
| 2012/0053622 | A1 | 3/2012 | Schulman |
| 2012/0101525 | A1 | 4/2012 | Jenson et al. |
| 2012/0158044 | A1 | 6/2012 | Jenson et al. |
| 2012/0211543 | A1 | 8/2012 | Euteneuer |
| 2012/0239085 | A1 | 9/2012 | Schlotterback et al. |
| 2013/0012381 | A1 | 5/2013 | Brown et al. |
| 2013/0110165 | A1 | 5/2013 | Burkhart et al. |
| 2014/0107700 | A1 | 4/2014 | Baird et al. |
| 2014/0257383 | A1 | 9/2014 | Lombardo et al. |
| 2014/0257385 | A1 | 9/2014 | Lunn et al. |
| 2014/0277133 | A1 | 9/2014 | Foerster |
| 2015/0173739 | A1 | 6/2015 | Rodriguez et al. |
| 2015/0250471 | A1 | 9/2015 | Nason et al. |
| 2016/0338688 | A1 | 11/2016 | Nason et al. |
| 2018/0042601 | A1 | 2/2018 | Baird et al. |
| 2020/0205804 | A1 | 7/2020 | Baird et al. |
| 2022/0117596 | A1 | 4/2022 | Baird et al. |
| 2022/0117597 | A1 | 4/2022 | Nason et al. |

FOREIGN PATENT DOCUMENTS

| | | | |
|---|---|---|---|
| JP | 2011092742 | A | 5/2011 |
| JP | 2012052262 | A | 3/2012 |
| JP | 2014061379 | A | 4/2014 |
| JP | 2018520819 | A | 8/2018 |
| WO | WO-2006074550 | A1 | 7/2006 |
| WO | WO-2008100534 | A2 | 8/2008 |
| WO | WO-2013096224 | A1 | 6/2013 |

OTHER PUBLICATIONS

"U.S. Appl. No. 15/797,980, Notice of Allowance dated Dec. 27, 2019", 9 pgs.

"U.S. Appl. No. 15/797,980, Response filed Dec. 4, 2019 to Non Final Office Action dated Sep. 5, 2019", 7 pgs.

"U.S. Appl. No. 16/815,507, Preliminary Amendment filed Mar. 12, 2020", 6 pgs.

"Australian Application Serial No. 2016268130, Response filed Sep. 6, 2019 to First Examination Report dated Aug. 22, 2019", 1 pg.

"Japanese Application Serial No. 2018-512839, Notification of Reasons for Refusal dated Mar. 24, 2020", (W/ English Translation), 8 pgs.

"Japanese Application Serial No. 2018-512839, Response filed Jun. 12, 2020 to Notification of Reasons for Refusal dated Mar. 24, 2020", (W/ English Translation), 19 pgs.

"U.S. Appl. No. 15/797,980, Non Final Office Action dated Sep. 5, 2019", 10 pgs.

"U.S. Appl. No. 14/052,624, Examiner Interview Summary dated Jul. 6, 2017", 3 pgs.

"U.S. Appl. No. 14/052,624, Final Office Action dated Mar. 29, 2017", 12 pgs.

"U.S. Appl. No. 14/052,624, Non Final Office Action dated Jun. 15, 2017", 11 pgs.

"U.S. Appl. No. 14/052,624, Non Final Office Action dated Sep. 7, 2016", 10 pgs.

"U.S. Appl. No. 14/052,624, Notice of Allowance dated Oct. 12, 2017", 8 pgs.

"U.S. Appl. No. 14/052,624, Notice of Non-Compliant Amendment dated Mar. 8, 2016", 2 pgs.

"U.S. Appl. No. 14/052,624, Notice of Non-Compliant Amendment dated Apr. 14, 2016", 2 pgs.

"U.S. Appl. No. 14/052,624, Response filed Feb. 29, 2016 to Restriction Requirement dated Aug. 31, 2015", 6 pgs.

"U.S. Appl. No. 14/052,624, Response filed May 22, 2017 to Final Office Action dated Mar. 29, 2017", 8 pgs.

"U.S. Appl. No. 14/052,624, Response filed Jun. 14, 2016 to Notice of Non-Compliant Amendment dated Apr. 14, 2016", 6 pgs.

"U.S. Appl. No. 14/052,624, Response filed Jun. 29, 2017 to Non Final Office Action dated Jun. 15, 2017", 8 pgs.

"U.S. Appl. No. 14/052,624, Response filed Nov. 30, 2016 to Non Final Office Action dated Sep. 7, 2016", 8 pgs.

"U.S. Appl. No. 14/052,624, Restriction Requirement dated Aug. 31, 2015", 7 pgs.

"U.S. Appl. No. 15/161,234, Final Office Action dated May 9, 2019", 13 pgs.

"U.S. Appl. No. 15/161,234, Non Final Office Action dated Oct. 4, 2018", 12 pgs.

"U.S. Appl. No. 15/161,234, Notice of Allowance dated Jul. 29, 2019", 8 pgs.

"U.S. Appl. No. 15/161,234, Preliminary Amendment filed Jun. 7, 2017", 7 pgs.

"U.S. Appl. No. 15/161,234, Response filed Jan. 4, 2019 to Non Final Office Action dated Oct. 4, 2018", 11 pgs.

"U.S. Appl. No. 15/161,234, Response filed Jun. 19, 2019 to Final Office Action dated May 9, 2019", 11 pgs.

"U.S. Appl. No. 15/797,980, Preliminary Amendment filed Oct. 31, 2017", 6 pgs.

"Australian Application Serial No. 2013328971, First Examiners Report dated Jun. 16, 2016", 3 pgs.

"Australian Application Serial No. 2013328971, Response filed Dec. 16, 2016 to First Examiners Report dated Jun. 16, 2016", 22 pgs.

"Australian Application Serial No. 2016268130, First Examination Report dated Aug. 22, 2019", 2 pgs.

"Australian Application Serial No. 2017202516, First Examination Report dated Mar. 26, 2018", 3 pgs.

"Australian Application Serial No. 2017202516, Response filed Apr. 29, 2018 to First Examination Report dated Mar. 26, 2018", 10 pgs.

"European Application Serial No. 13845008.5, Extended European Search Report dated Mar. 23, 2017", 4 pgs.

"European Application Serial No. 13845008.5, Extended European Search Report dated May 17, 2016", 8 pgs.

"European Application Serial No. 13845008.5, Response filed Jun. 12, 2017 to Communication pursuant to Article 94(3) EPC dated Mar. 23, 2017", 6 pgs.

"European Application Serial No. 13845008.5, Response filed Nov. 20, 2015 to Communication pursuant to Rules 161(1) and 162 EPC dated May 27, 2015", 6 pgs.

(56) References Cited

OTHER PUBLICATIONS

"European Application Serial No. 13845008.5, Response filed Nov. 29, 2016 to Extended European Search Report dated May 17, 2016", 27 pgs.

"European Application Serial No. 16800570.0, Extended European Search Report dated Jan. 22, 2019", 10 pgs.

"European Application Serial No. 16800570.0, Response Filed Aug. 19, 2019 Extended European Search Report dated Jan. 22, 2019", 8 pgs.

"European Application Serial No. 16800570.0, Response filed Aug. 20, 2018 to Office Action dated Feb. 8, 2018", 9 pgs.

"European Application Serial No. 18156124.2, Extended European Search Report dated May 8, 2018", 6 pgs.

"European Application Serial No. 18156124.2, Response Filed Dec. 20, 2018 to Extended European Search Report dated May 8, 2018", 22 pgs.

"International Application Serial No. PCT/US2013/064706, International Search Report dated Mar. 10, 2014", 4 pgs.

"International Application Serial No. PCT/US2013/064706, Written Opinion dated Mar. 10, 2014", 6 pgs.

"International Application Serial No. PCT/US2016/033680, International Preliminary Report on Patentability dated Dec. 7, 2017", 8 pgs.

"International Application Serial No. PCT/US2016/033680, International Search Report dated Sep. 12, 2016", 5 pgs.

"International Application Serial No. PCT/US2016/033680, Written Opinion dated Sep. 12, 2016", 6 pgs.

"Japanese Application Serial No. 2015-536971, Office Action dated Aug. 8, 2017", w/English Translation, 6 pgs.

"Japanese Application Serial No. 2015-536971, Response filed Oct. 20, 2017 to Office Action dated Aug. 8, 2017", w/English Translation and English Claims, 10 pgs.

Inui, et al., "Regeneration of Rotator Cuff Tear Using Electrospun Poly (D,L-Lactide-Co-Clycolide) Scaffolds in a Rabbit Model", Arthroscopy: The Journal of Arthroscopic and Related Surgery, (Dec. 2012), 1790-1799.

"U.S. Appl. No. 17/565,425, Preliminary Amendment filed Jan. 24, 2022", 5 pgs.

"U.S. Appl. No. 17/565,428, Preliminary Amendment filed Jan. 20, 2022", 6 pgs.

"European Application Serial No. 16800570.0, Communication Pursuant to Article 94(3) EPC dated Aug. 2, 2022", 5 pgs.

\* cited by examiner

SYSTEMS AND METHODS FOR REPAIRING SOFT TISSUES

This application claims the benefit under 35 U.S.C. 119(e) of the filing date of Provisional U.S. Application Ser. No. 62/165,822, entitled Suture Anchoring Systems and Materials, filed on May 22, 2015, and is related to commonly assigned U.S. patent application Ser. No. 14/052,624, entitled Systems and Methods for Repairing Soft Tissues Using Nanofiber Material, filed on Oct. 11, 2013. The foregoing applications are each herein expressly incorporated by reference, in their entirety.

BACKGROUND OF THE INVENTION

Rotator cuff repair is the most common surgical repair performed in the shoulder, with more than 270,000 repairs performed annually in the United States, as of 2006, with that number expected to increase annually with concurrent increase in the aging population. Advances in rotator cuff repair technique have focused principally on transition from open repair, to mini-open repair, and more recently to fully arthroscopic repair. Moreover, advances have been made in suture patterns or arthroscopic repairs to better recreate the natural footprint insertion of the rotator cuff to improve time-zero mechanical properties, and in hopes of improving the healing rates.

In spite of improvements in surgical technique, healing rates as evidenced by postoperative ultrasound or MRI have varied widely, ranging from 91% healing rates in small tears to healing rates of only 10% in the largest tears. It is believed that healing rates are low due to the inadequate re-creation of the natural anatomic bone-tendon interface.

Various techniques have been employed to improve interface healing, including mesenchymal stem cells, xenograft, allograft, and acellular nanofiber scaffolds. Advances in nanofiber technology may hold promise in improving the bone-tissue interface healing of many soft tissue injuries, and have several advantages over other proposed methods. Issues of procurement, scalability, ease of use, and integration with currently performed surgical repair methods favor the nanofiber scaffolds. As noted in Inui et al. ("Regeneration of Rotator Cuff Tear Using Electrospun Poly (D. L-Lactide-Co-Glycolide) Scaffolds in a Rabbit Model"), *The Journal of Arthroscopic and Related Surgery*, Vol. 28, No. 12 (December), 2012; pp. 1790-1799), nanofiber size can range up to at least about 14 μm in the orthopedic field.

Usage of acellular augmentation devices have been evaluated in animal models, demonstrating safety to the animal and effectiveness in improving the soft tissue healing. Yokoya et al. ("Tendon-Bone Insertion Repair and Regeneration Using Polyglycolic Acid Sheet in the Rabbit Rotator Cuff Injury Model", *American Journal of Sports Medicine*, Vol. 36, no. 7, pp. 1298-1309, 2008) used a polyglycolic acid (PGA) sheet to augment rotator cuff repairs of infraspinatus tendons in Japanese white rabbits, showing histological improvement in fibrocartilage layering and a slight improvement in tensile strength when compared to control tendons. Funakoshi et al. ("Rotator Cuff Regeneration Using Chitin Fabric as an Acellular Matrix", *Journal of Shoulder and Elbow Surgery*, Vol. 15, No. 1, pp. 112-118, 2006) demonstrated increased fibroblast presence and collagen formation when synthetic extracellular matrix was surgically applied to rotator cuff tears in Japanese white rabbits. MacGillivray et al. ("Biomechanical Evaluation of a Rotator. Cuff Defect Model Augmented with a Bioresorbable Scaffold in Goats", *Journal of Shoulder and Elbow Surgery*, Vol. 15, No. 5, pp. 639-644, 2006) used polylactic acid patches in goats, showing safety to the animal but minimal difference between the treated and control groups. A similar experiment using a woven poly-L-lactide device was performed by Derwin et al. ("Rotator Cuff Repair Augmentation in a Canine Model with Use of a Woven Poly-L-Lactide Device", *Journal of Bone and Joint Surgery A*, Vol. 91, No, 5, pp. 11594171, 2009) in a dog model. A portion of each infraspinatus tendon was removed from the rotator cuff and then repaired in both shoulders. In one shoulder, a woven poly-L-lactide device was placed over the repair. In the other shoulder, the repair was left unaugmented. The augmented rotator cuff repair resulted in fewer tendon retractions, greater strength, and increased stiffness when compared to the contralateral untreated rotator cuff repairs.

In an attempt to improve the healing of the tissue-bone interface, acellular nanofiber scaffolds have been studied. Nanofiber scaffolds are typically made from materials with well-known biologic properties. For example, poly-lactide-co-glycolide (PLGA) is a material commonly used in absorbable sutures and medical devices. PLGA can be fashioned via electrospinning into nanofiber sheets, which in turn can be interposed between a torn tendon and the underlying bone attachment site during surgical tissue repair. Additionally, other polymers that are non-absorbable have been used as nanofiber scaffolds as well. When used in this manner it should be noted that the nanofiber is not acting as a structural graft under tension. The interposed fibers are used only as a scaffold to support ingrowth of host cells.

Moffat et al ("Novel Nanofiber-Based Scaffold for Rotator Cuff Repair and Augmentation", *Tissue Eng Part A*, Vol. 14, pp. 1-12, 2008) used an in vivo model to study the potential for an aligned nanofiber sheet to promote fibroblast formation and improved mechanical properties. They found that "mechanical properties of the aligned nanofiber scaffolds were significantly higher than those of the unaligned, and although the scaffolds degraded in vitro, physiologically relevant mechanical properties were maintained. These observations demonstrate the potential of the PLGA nanofiber-based scaffold system for functional rotator cuff repair. Moreover, nanofiber organization has a profound effect on cellular response and matrix properties, and it is a critical parameter for scaffold design." Some controversy exists over the best nanofiber architecture: monophasic, biphasic, or even triphasic.

Implantation of sheets of material as studied by Moffat, Derwin, MacGillivray, Funakoshi, and others requires an open surgical procedure. The current standard-of-care for rotator cuff repair is an arthroscopic procedure, growing from less than ten percent of all rotator cuff repairs in 1996 to almost sixty percent of all rotator cuff repairs in 2006. The trend has continued in the past 6 years, with current estimates suggesting that greater than 85% of rotator cuff repairs are performed arthroscopically. Further improvements to the procedure that are potentially offered by devices and/or materials as described by Moffat must be compatible with arthroscopic implantation methods in order to be widely accepted.

Rotator cuff repair surgery has evolved from predominately being performed with an open procedure to an arthroscopic procedure during the past 15 years. The current state-of-the art arthroscopic procedure generally utilizes one of the following approaches:

a) as shown in FIG. 1, a single row of suture anchors 1 lying underneath the rotator cuff tendon 2 with sutures passed up through the tendon and securely tied to anchor the tendon to the bone 3;

b) as shown in FIG. 2, a double row of suture anchors 1 lying underneath the rotator cuff tendon 2 with sutures passed up through the tendon and securely tied to anchor the tendon to the bone 3;

c) as shown in FIG. 3, a single row of suture anchors 1 lying underneath the rotator cuff tendon 2 with sutures passed up through the tendon, securely tied, with suture from knots extending laterally over the tendon and secured to the bone 3 with a knotless suture anchor 4 that is outside the margin of the tendon.

There are no prospective, randomized published studies that show a difference in outcome between the three procedure groups listed above and depicted in FIGS. 1-3, and in spite of improvements in surgical technique, failure rates (defined as the tendon not healing to the bone) as evidenced by postoperative ultrasound or MRI have varied widely, range from 9% in small tears, to 90% in the largest tears. It is believed that failure to heal is due to the inadequate re-creation of the natural anatomic bone-tendon interface.

Various techniques have been employed to improve interface healing, including mesenchymal stem cells, xenografts, allografts, and acellular nanofiber scaffolds. Advances in nanofiber technology may hold promise in improving the bone-tissue interface healing of many soft tissue injuries, and have several advantages over other proposed methods. Issues of procurement, scalability, ease of use, and integration with currently performed surgical repair methods favor the nanofiber scaffolds.

A product that combines the current arthroscopically-placed suture anchor implants with a nanofiber scaffold, as disclosed and described herein, will allow the surgeon to repair the rotator cuff using current arthroscopic methods.

SUMMARY OF THE INVENTION

This invention comprises a wicking component integrated into an arthroscopically deployable suture anchor, and is intended to improve soft tissue-to-bone repair. Once deployed, the fibrous wick component extends from within the bone tunnel, out of the hole, and to the bone-tendon interface on the bone surface. The implant includes pre-loaded sutures that are passed through the soft tissue, and knots are tied to secure the tissue against the bone, sandwiching the wick material between the bone and tissue. Alternatively, the suture anchor can be knotless, with the capability to accept and secure a suture or sutures that have already been passed through soft tissue prior to loading into the anchor and deploying the anchor in the bone.

The wick component is ideally a polymeric fibrous or tissue-based scaffold that provides several advantages over current repair techniques and devices. One such advantages is that the wick material in the inventive system provides a pathway for cells (autologous bone marrow constituents and blood) to travel from within the bone to the soft tissue-bone interface, accelerating and promoting the healing response. Another advantage is that the inventive system provides a biomimetic structure that stimulates the extracellular matrix to encourage cell attachment and potentially improve the healing response.

Although the ideal wick component is described as a polymeric fibrous scaffold, other design variations of the wick can provide similar advantages. Any porous material that allows the transfer of bone marrow constituents and/or blood from the interior of the bone to the bone tissue interface will provide this advantage over current suture anchors.

In addition, the wick component does not need to be integrated into a suture anchor and installed when the suture anchor is deployed. For example, the wick component could be placed above or near a traditional suture anchor after it has been deployed. The wick component could attach to and be secured by the suture anchor (or its preloaded floating sutures), or it could incorporate features that secure it in or on the bone independently of the suture anchor. In either case, it would be positioned such that it provides a pathway for cells from within the bone to the bone soft tissue interface and the suture anchor provides the structural anchor point to secure the tissue against the bone.

Finally, the wick component may be used independently of a traditional suture anchor. The wick may be installed in or on the bone and be held in place by the overlying tissue itself, or it may incorporate features that secure it to the bone without floating sutures that secure the tissue against the bone.

The suture anchor with integrated wick or separate wick component may be deployed by either common arthroscopic or other surgical techniques.

More particularly, there is provided an anchoring system for securing soft tissue to bone. This system comprises an implant having an undeployed configuration and a deployed configuration, the implant being securable to adjacent bone when in the deployed configuration. A wick is connected to the implant, the wick comprising a first portion having an extended surface area which is movable between a retracted undeployed configuration and an extended deployed configuration and a second portion connecting the first portion to the implant, the wick first portion being comprised of a material adapted to provide a pathway for cells to travel from within the bone to an interface between the bone and soft tissue to promote healing at the bone and soft tissue interface. A shielding structure is disposed about and protects the wick during insertion of the wick into a position adjacent to a desired bone and soft tissue interface.

In certain embodiments, the shielding structure comprises a sheath, which may include a plurality of apertures therein. The system further comprises an inserter comprising a sleeve which holds the implant and the wick in place in their undeployed configurations prior to deployment, as well as a proximal actuator for deploying the implant.

When the inserter is withdrawn proximally, the wick first portion is moved to its extended deployed configuration. The wick comprises a foldable thin scaffold sheet formed of a polymer having aligned fibers disposed therein, the wick first portion comprising a paddle portion and the wick second portion comprising an elongated portion. The wick second portion is engaged with a corresponding elongated portion of the sheath when the wick is in its undeployed configuration.

When the wick paddle portion is in its extended deployed configuration, the paddle portion is adapted to be sandwiched between a bone surface and an adjacent soft tissue member, and the aligned fibers disposed therein are adapted to be aligned with the direction of travel of cells from bone marrow in the bone surface to the soft tissue. The wick may preferably be comprised of an 85/15 L lactide/glycolide polymer, electrospun into said thin scaffold sheet. The implant may comprise an all-suture anchor.

The second wick portion is wrapped around a shaft of the inserter prior to deployment of the second wick portion. The sheath may be fabricated from a thin sheet of PEEK.

In other embodiments, the shielding structure may comprise a two piece anchor. The two piece anchor comprises a distal anchor piece and a proximal anchor piece, and the wick is disposed between the distal and proximal anchor pieces before deployment of the first wick portion. More particularly, the second wick portion is disposed between the distal and proximal anchor pieces before deployment of the first wick portion. The system further comprises an inserter comprising a sleeve which holds the first wick portion in place in its undeployed configuration prior to deployment.

In another aspect of the invention, there is provided an insert for use in a soft tissue anchoring system, comprising a wick adapted to be implanted with an implant at a procedural site having a bone and soft tissue interface. The wick comprises a first portion having an extended surface area which is movable between a retracted undeployed configuration and an extended deployed configuration and a second portion connected to the first portion, the wick first portion being comprised of a material adapted to provide a pathway for cells to travel from within the bone to an interface between the bone and soft tissue to promote healing at the bone and soft tissue interface. The system, which is adapted for use with any suitable available implant, also comprises a shielding structure disposed about and protecting the wick during insertion of the wick into a position adjacent to a desired bone and soft tissue interface, the shielding structure being connected to the wick second portion. The shielding structure comprises a two piece anchor, which comprises a distal anchor piece and a proximal anchor piece, and the wick is disposed between the distal and proximal anchor pieces before deployment of the first wick portion. More particularly, the second wick portion is disposed between the distal and proximal anchor pieces before deployment of the first wick portion.

In still another aspect of the invention, there is disclosed a method for securing soft tissue to bone, which comprises steps of inserting an implantable anchor into a desired bone site and deploying the anchor to secure the anchor to the bone at the bone site. An inserter is utilized to deploy an extended wick surface against the bone. The soft tissue is approximated to the bone so that the soft tissue engages the extended wick surface and the extended wick surface is sandwiched between the bone and the soft tissue.

The invention, together with additional features and advantages thereof, may best be understood by reference to the following description taken in conjunction with the accompanying illustrative drawing.

DESCRIPTION OF THE PREFERRED EMBODIMENT

Referring now more particularly to the drawings, it is noted that the embodiments shown and described herein comprise a wick component integrated into a suture anchor that is deployed using current arthroscopic methods. In particular, the described embodiments are usable with and build upon the SURELOCK™ all-suture anchor, currently marketed by the assignee of the present application, Cayenne Medical, Inc., of Scottsdale, Ariz., The SURELOCK suture anchor is disclosed, for example, in commonly assigned U.S. patent application Ser. No. 14/639,943, entitled All-Suture Suture Anchor Systems and Methods, filed on Mar. 5, 2015 and presently pending. An all-suture suture anchor is also disclosed in commonly assigned U.S. patent application Ser. No. 14/589,960, entitled All-Suture Suture Anchor Systems and Methods, filed on Jan. 5, 2015, and also presently pending. Both of these prior applications are herein expressly incorporated by reference, in their entirety. Of course, other types of suture anchors could be used in connection with the invention, as those of ordinary skill in the art will discern.

The all-suture anchor provides the structural support for the floating sutures that secure the tissue against the bone in the present invention. The PEEK (Polyether ether ketone) and wick components provide the wick pathway from the cancellous bone marrow to the bone tissue interface.

Figure 1:
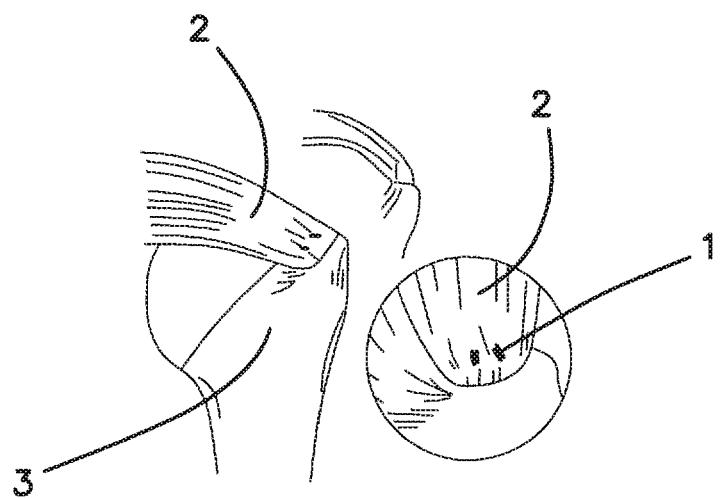
FIG. 1 is a schematic drawing of a first prior art approach for repairing a rotator cuff.
Figure 2:
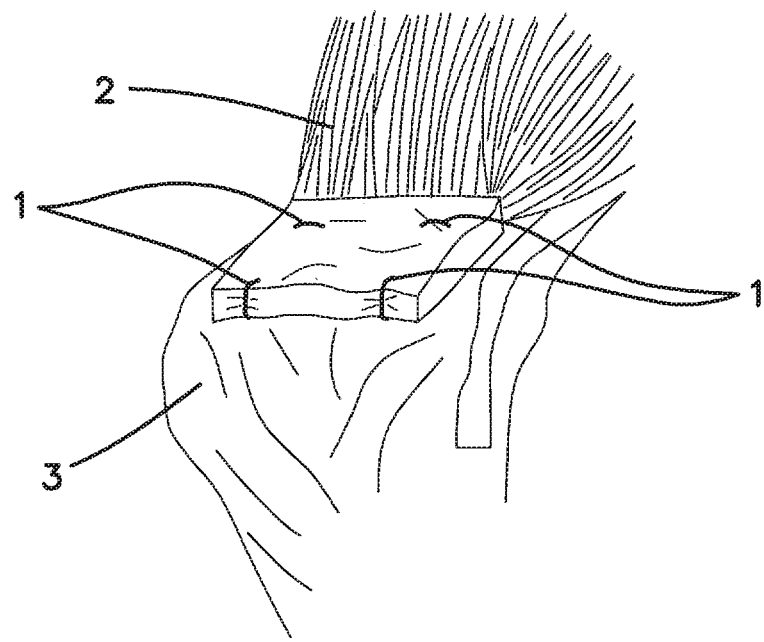
FIG. 2 is a schematic drawing of a second prior art approach for repairing a rotator cuff.
Figure 3:
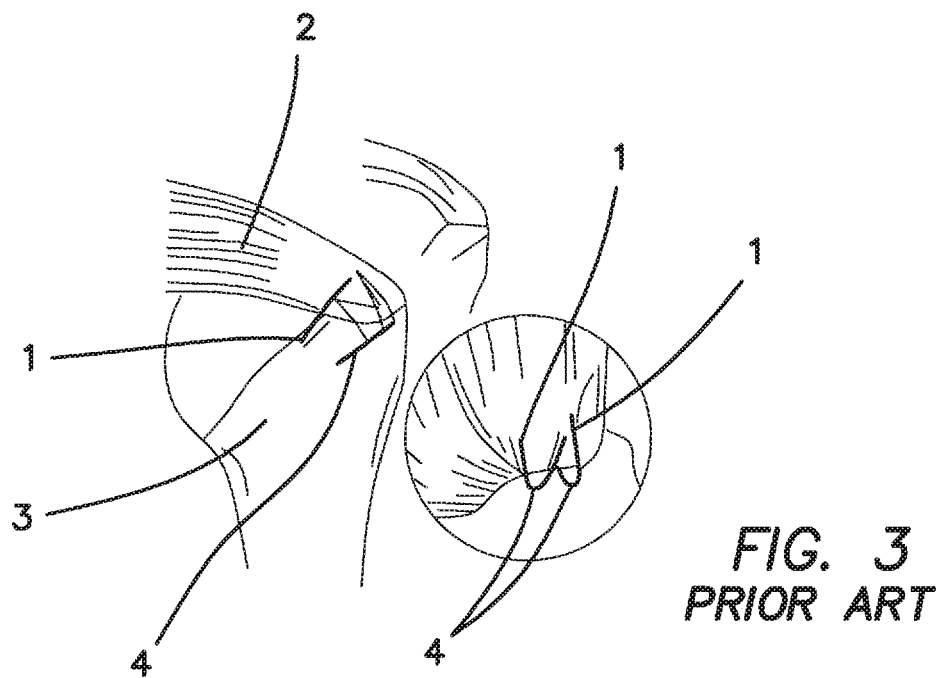
FIG. 3 is a schematic drawing of a third prior art approach for repairing a rotator cuff.
Figure 4:
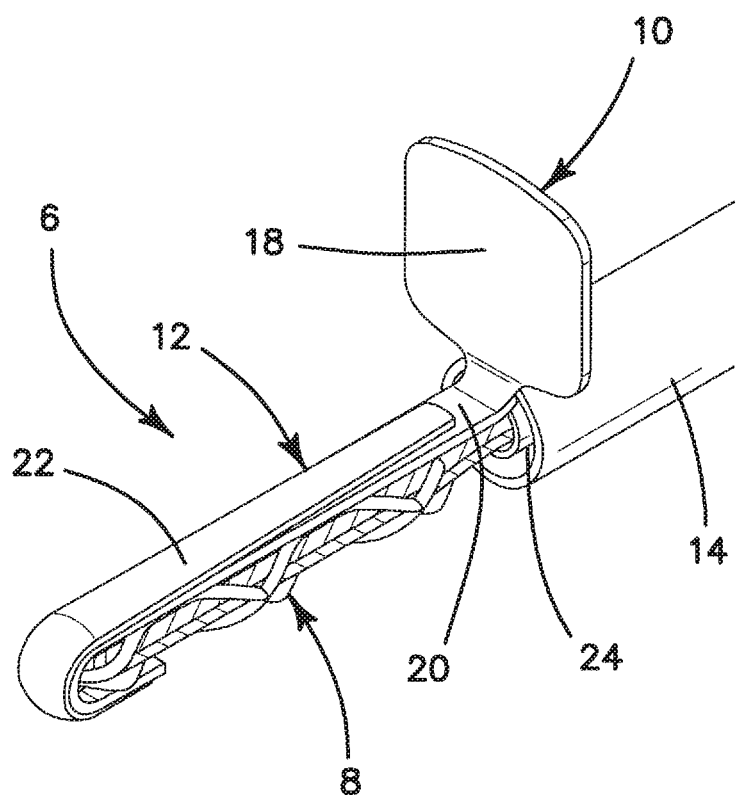
FIG. 4 is an isometric view of a sheath wick construct in accordance with the principles of the present invention.

A sheath wick construct 6 is illustrated in FIGS. 4-10. This embodiment adds three primary elements to the aforementioned SURELOCK all-suture anchor 8 and inserter. One of these three elements is a wick component 10. Also present are a sheath 12 for protecting the wick 10 during insertion and deployment of the all-suture anchor 8, as well as an outer sleeve or deployment tube sleeve 14 to house the construct and provide a depth limiter. FIG. 4 illustrates the sleeve 14 in a fully retracted orientation, with the wick 10 in a deployed orientation.

The wick component 10 in this embodiment may be made from an 85/15 L lactide/glycolide polymer, electrospun into a thin scaffold sheet. Both sides of the sheet comprise aligned microfibers 16 of material (FIG. 5), aligned in the direction shown, lengthwise along a longitudinal axis of the wick. As illustrated, the wick 10 comprises a paddle portion 18, which is adapted to be oriented substantially orthogonally relative to a longitudinal axis of the device 6 and is planar in configuration, and an elongated portion 20, which is adapted to be disposed longitudinally relative to the device 6, and in engagement with a corresponding elongated portion 22 of the sheath 12, as shown in FIG. 4. When deployed, the fibers 16 are aligned with the direction of travel of the cells from the bone marrow to the surface, as well as with the linearly oriented fibers of the soft tissue. The term "microfiber" is intended to include nanofibers, as well as other small diameter fibers up to and including approximately $1 \times 10^{-4}$ m, and more preferably in the range of approximately 0.1-20 µm.

Figure 5:
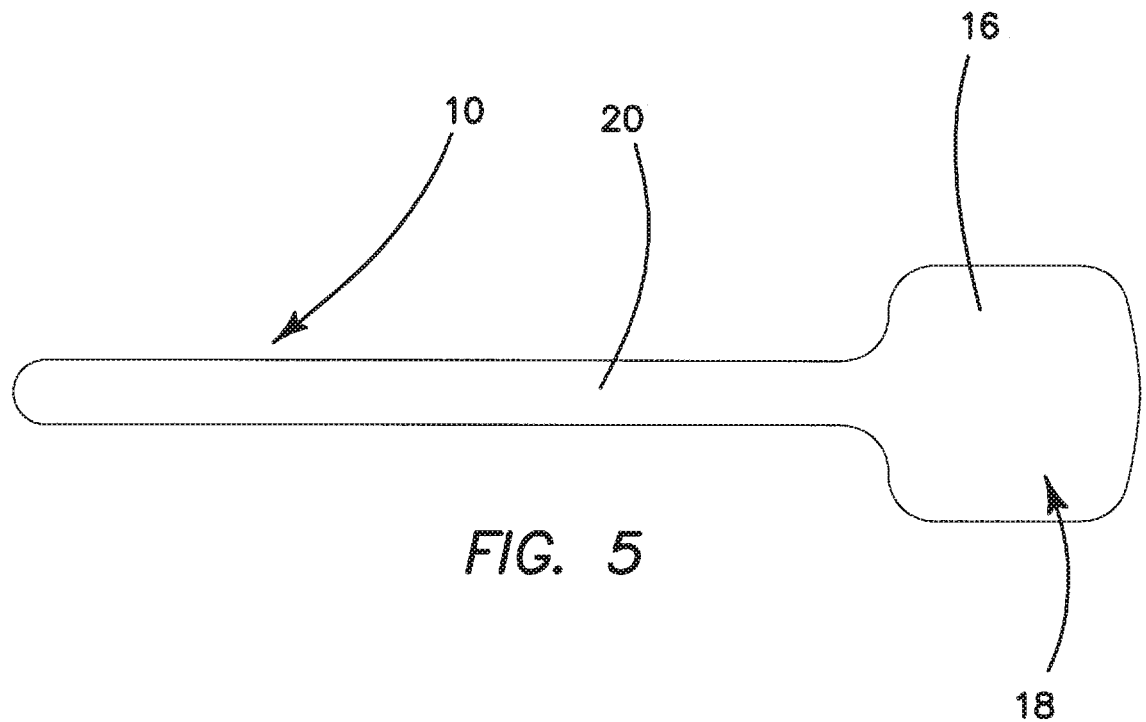
FIG. 5 is a view illustrating the flat pattern of the wick component of FIG. 4.

The sheet material is cut into a shape similar to that shown in FIG. 5. The long, narrow elongated portion 20 is wrapped around the tip of the all suture anchor 8 prior to deployment, and the paddle portion 18 is wrapped around inserter shaft 24, inside the deployment tube sleeve 14. After the anchor is deployed, the elongated portion 20 runs from the bottom of the bone tunnel, alongside the all-suture anchor 8, up to the bone surface. The paddle portion 18 lies on the bone surface, underneath the soft tissue being repaired.

Figure 6:
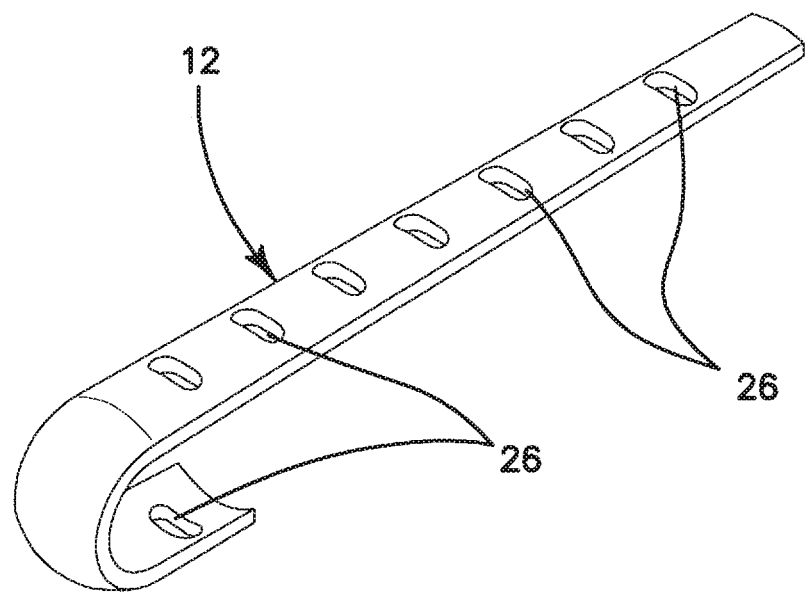
FIG. 6 is an isometric view of the sheath of FIG. 4.

The sheath 12, in one embodiment, is made from a thin sheet of PEEK or other suitable material, which is cut into the illustrated shape, and runs along the length of the anchor on top of the wick 10, wrapping around the tip of the inserter. The function of the sheath 12 is to protect the fragile wick 10 as the anchor is inserted into the bone tunnel and during deployment of the all-suture anchor 8. The sheath 12 may have holes or slots 26 cut into it, as shown in FIG. 6, to improve fluid communication between the bone marrow and the wick 10 or to improve the pull-out force of the anchor.

Figure 7:
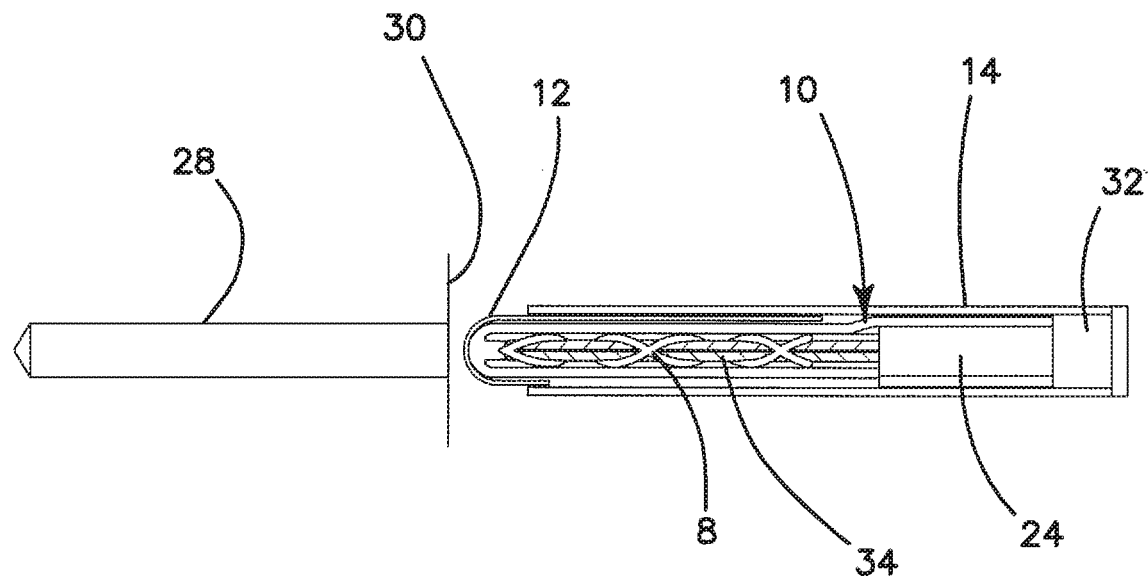
FIG. 7 is a cross-sectional view of the sheath wick anchor embodiment shown in FIG. 4 adjacent to a bone tunnel prior to insertion thereof.
Figure 8:
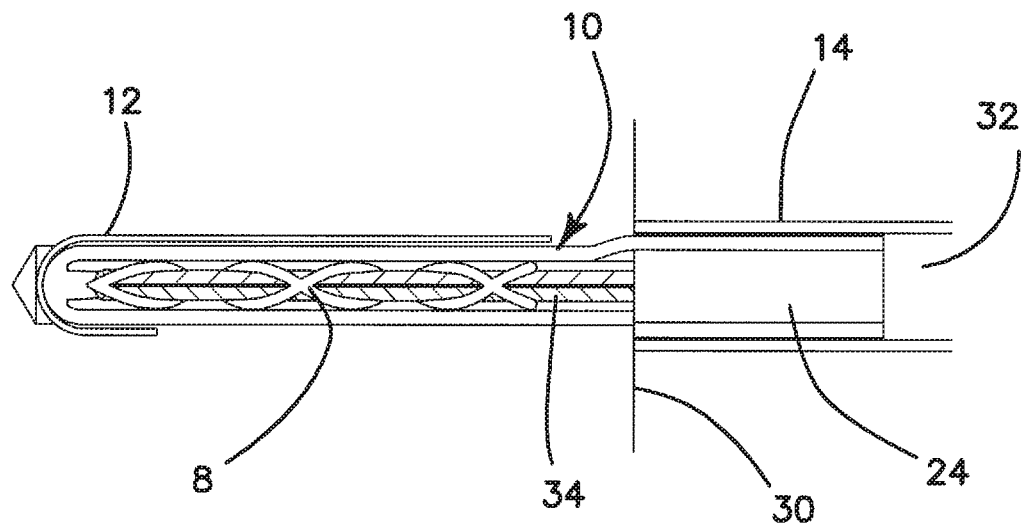
FIG. 8 is a cross-sectional view similar to FIG. 7, after the sheath wick anchor has been inserted into the bone tunnel.
Figure 9:
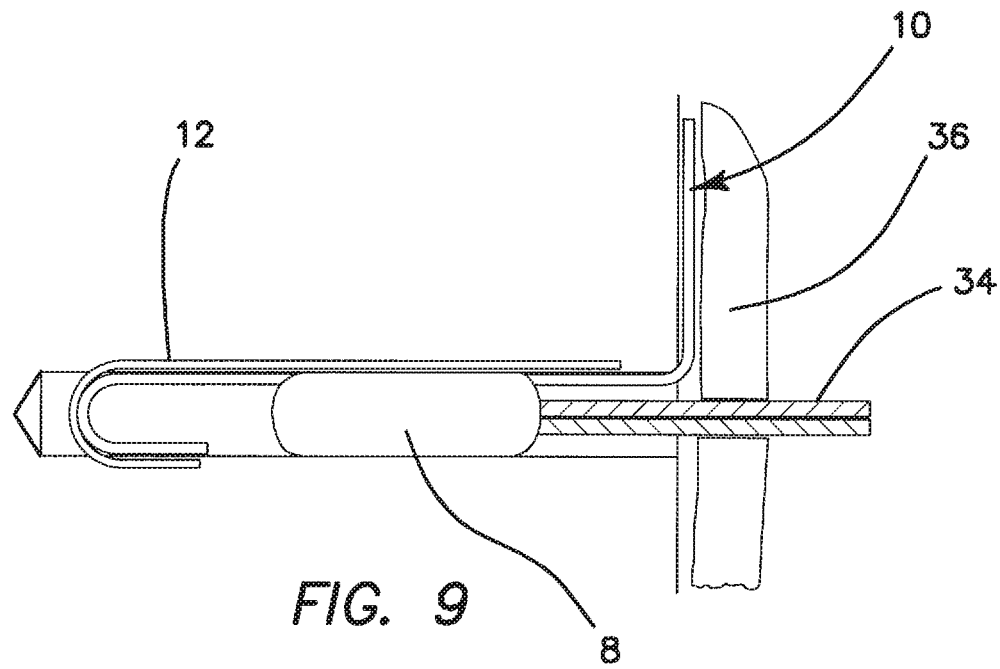
FIG. 9 is a cross-sectional view of the sheath wick anchor of FIG. 4 in a deployed configuration.
Figure 10:
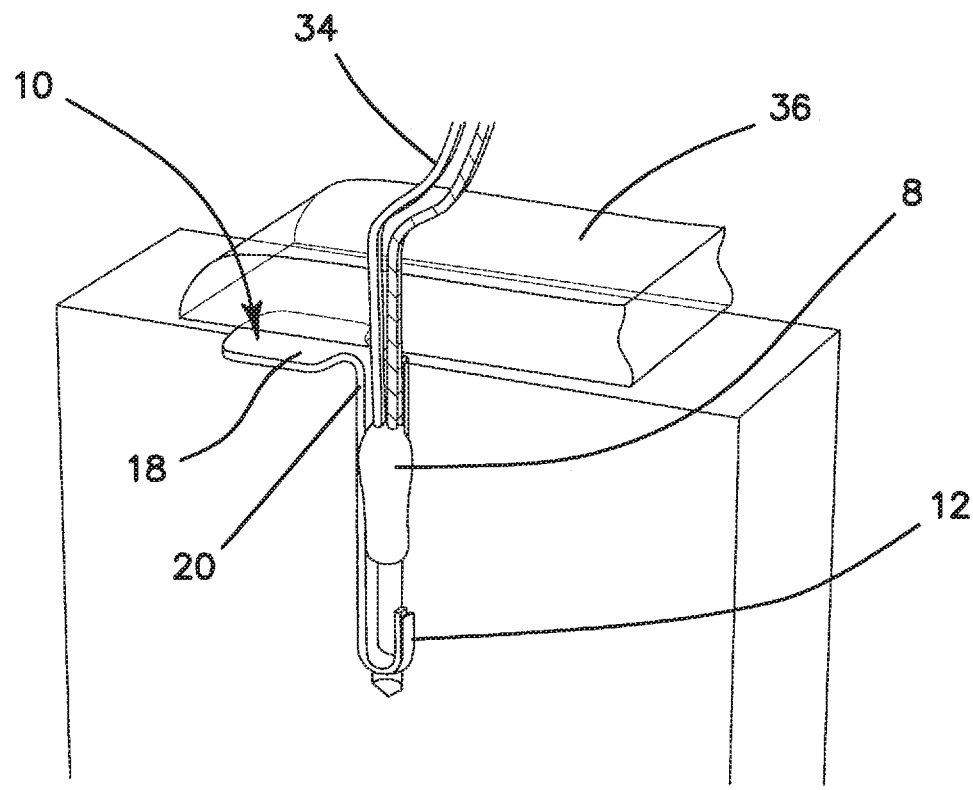
FIG. 10 is an isometric view of the deployed sheath wick construct of FIGS. 4-9.

The components are held in place by the deployment tube sleeve 14 prior to deployment, as shown in FIG. 7. The tip of the inserter (with the anchor 8) is placed into a bone tunnel 28. The end of the deployment tube sleeve 14 bottoms out against the bone surface 30. As the anchor is malleted into the bone tunnel 28, the deployment tube sleeve 14 slides with respect to the inserter shaft 24 and stays stationary against the bone surface 30 (FIG. 8). The deployment tube sleeve bottoms out against the inserter handle 32, to act as a depth stop for the anchor construct 6. Once the anchor is inserted to the proper depth, the all-suture anchor 8 is deployed by turning the knob 32 on the inserter. The anchor is pulled upwardly by floating sutures 34 and expands to compress against the walls of the bone tunnel 28, securing it within the bone. Once it is fully deployed, the inserter is removed by pulling it away from the bone surface 30. The paddle portion 18 of the wick 10 is pulled out of the deployment tube sleeve 14 and can be folded down to sit on the surface of the bone 30, as shown in FIGS. 9 and 10. The wick 10 provides a pathway to move bone marrow constituents from the bone tunnel 28 up to the interface between the bone surface (below the paddle portion 18) and the soft tissue 36 (above the paddle portion 18).

The repair is completed by passing the floating sutures 34 through the soft tissue 36, and knots are tied to secure the soft tissue 36 against the bone 30, sandwiching the wick material 10 between the bone and tissue.

Figure 11:
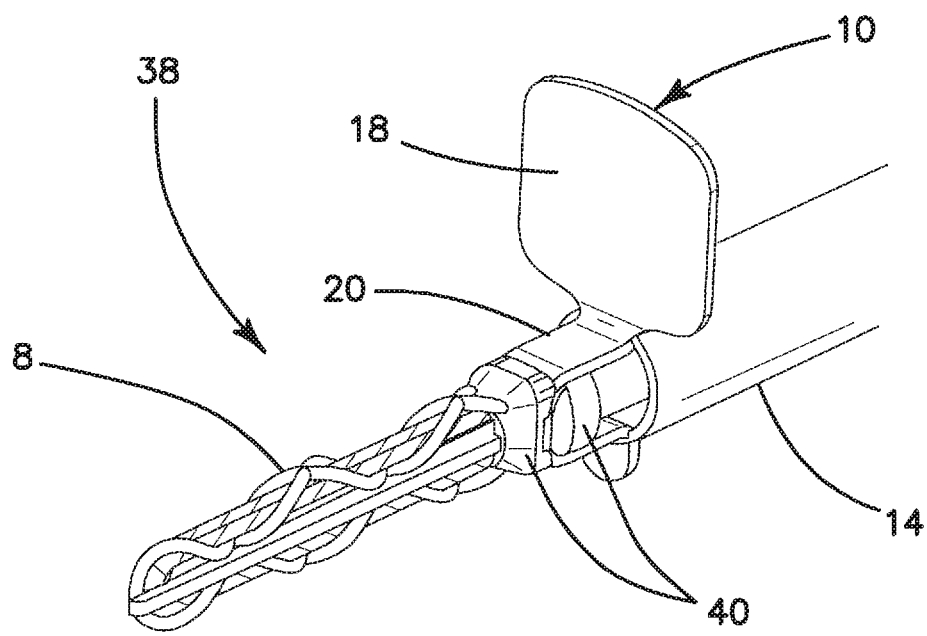
FIG. 11 is an isometric view of an alternative embodiment of the invention, comprising an all suture PEEK hybrid anchor construct.

FIGS. 11-16 illustrate another embodiment of the present invention, namely a PEEK anchor hybrid construct 38. When describing this embodiment, those elements which correspond to elements described in connection with the embodiment of FIGS. 1-10 are denoted by corresponding reference numerals in the drawings. As noted above in connection with construct 6, the construct 38 also adds three primary components to the existing SURELOCK all-suture anchor, or to other all-suture anchors which might be utilized in connection with the invention. In particular, the embodiment 38 includes a wick component 10, a two-piece PEEK barbed anchor 40, and a deployment tube sleeve 14. The two-piece barbed anchor 40 protects the wick 10 during insertion into the bone tunnel 28 and secures it after deployment. In FIG. 11, the deployment tube sleeve 14 is shown in its hilly retracted configuration.

The wick component 10 is preferably made from 85/15 L lactide/glycolide polymer, or other suitable material, electrospun into a thin scaffold sheet. Both sides of the sheet comprise aligned micro fibers of material 16, aligned in the illustrated direction along a longitudinal axis of the wick. When deployed, the fibers are aligned with the direction of travel of the cell from the bone marrow to the surface, as well as with the linearly oriented fibers of the soft tissue.

Figure 12:
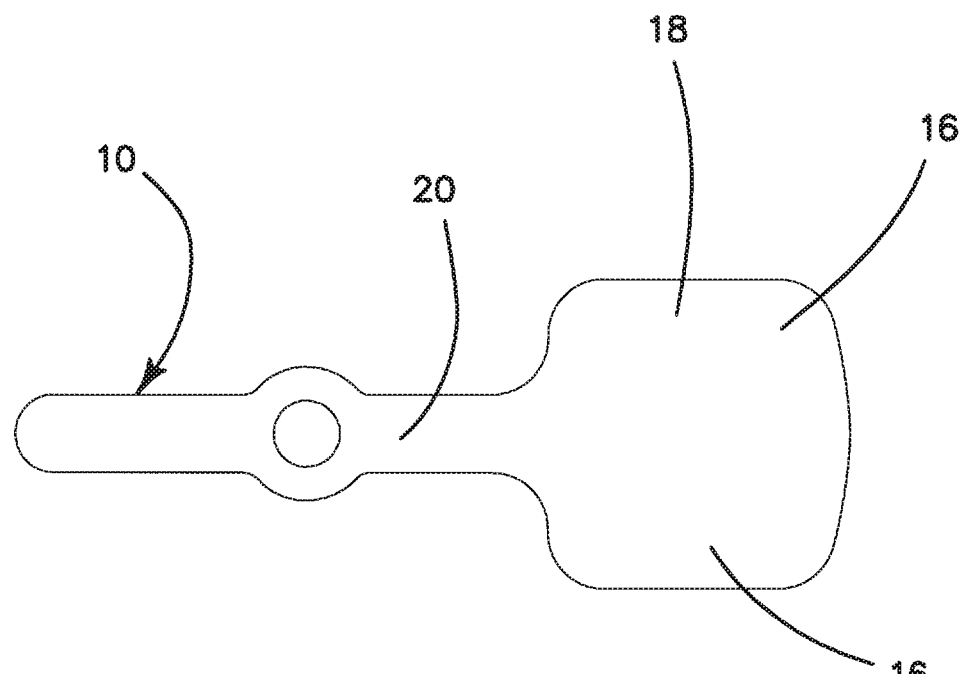
FIG. 12 is a view illustrating the flat pattern of the wick component of FIG. 11.

The sheet material for the wick 10 may be cut into a shape similar to that shown in FIG. 12. The narrow elongated end 20 is wrapped between the two PEEK anchor pieces 42 and 44, and the inserter shaft tip and floating sutures 34 run through the hole. The paddle portion 18 is wrapped around the inserter shaft 24, inside the deployment tube sleeve 14. After the anchor is deployed, the narrow elongated end 20 runs from the bone surface 30, down into the bone tunnel 28 alongside the PEEK anchor 40, and back up to the bone surface. The larger paddle portion 18 lies on the bone surface 30, underneath the soft tissue 36 being repaired.

The function of the PEEK barbed anchor pieces, including the distal piece 42 and the proximal piece 44 are to protect the fragile wick material 10 as the anchor is inserted into the bone tunnel 28. The distal anchor piece 42 enlarges the hole 28 as it is inserted to make room for the narrow strip 20 of wick material. Once the anchor is in place, the wick 10 is captured between the distal and proximal anchor pieces 42, 44, respectively, to secure it in place in the bone tunnel. The PEEK anchor pieces also compress against the sides of the bone tunnel 28 and add to the pull-out strength of the all-suture anchor alone, especially in soft bone.

Figure 13:
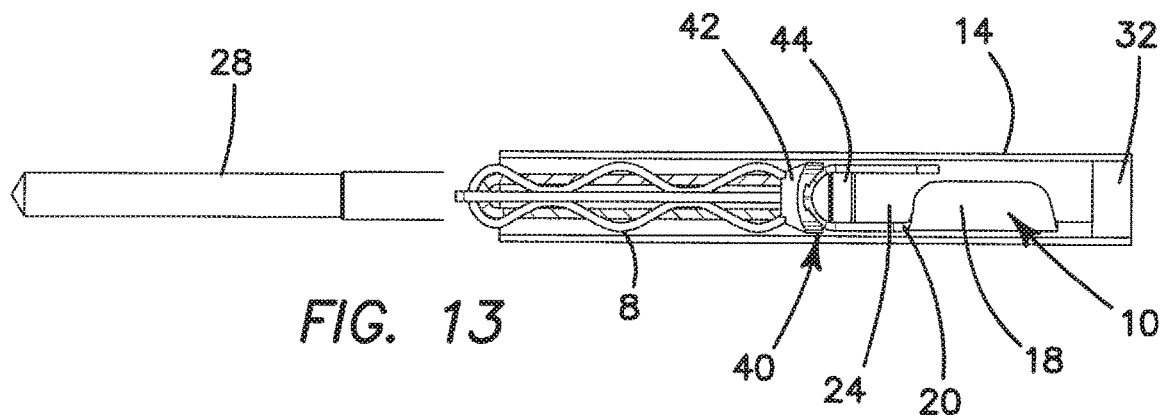
FIG. 13 is a cross-sectional view of the hybrid anchor construct of FIG. 11, disposed adjacent to a bone tunnel prior to insertion.
Figure 14:
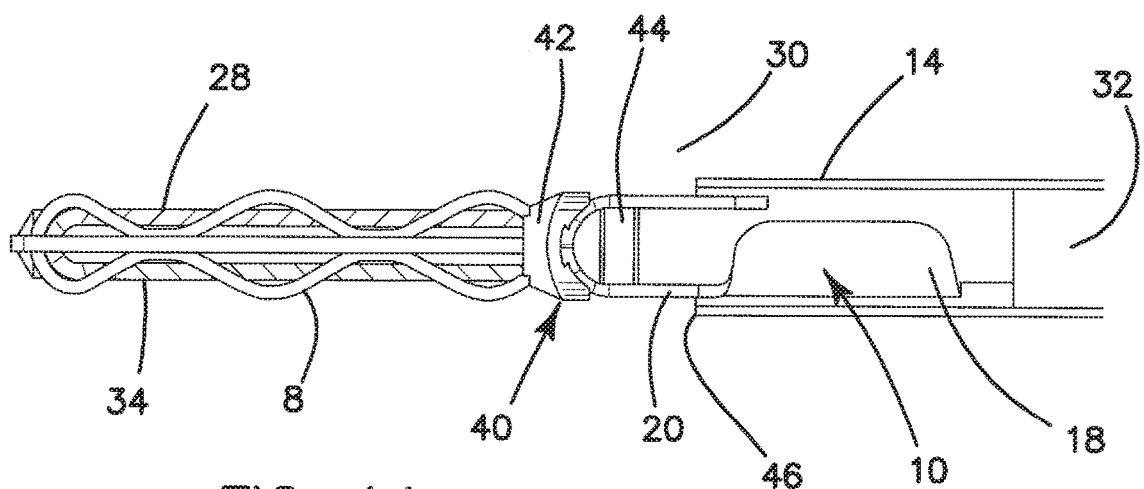
FIG. 14 is a cross-sectional view similar to FIG. 13, after the hybrid anchor has been inserted into the bone tunnel.
Figure 15:
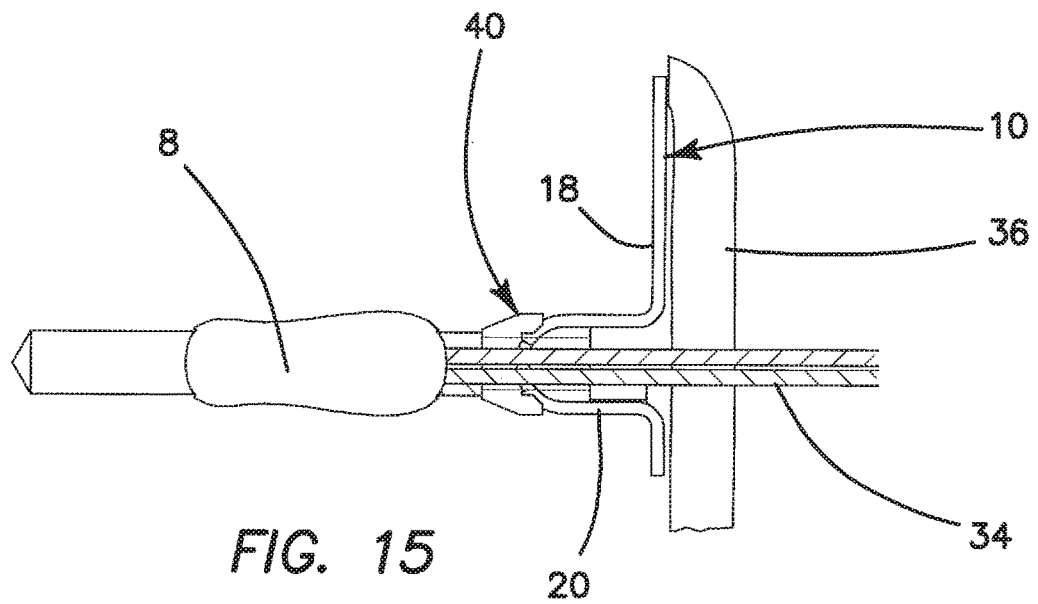
FIG. 15 is a cross-sectional view of the hybrid anchor in a deployed configuration.

The components are held in place by a deployment tube sleeve 14 prior to deployment, as shown in FIG. 13. The tip of the inserter (with the anchor) is placed into the bone tunnel 28, as shown in FIG. 14. The end 46 of the deployment tube sleeve 14 bottoms out against the bone surface 30. As the anchor is malleted into the bone tunnel 28, the deployment tube sleeve 14 slides with respect to the inserter shaft 24 and stays stationary against the bone surface 30, as also shown in FIG. 14. The deployment tube sleeve 14 bottoms out against the inserter handle 32 to act as a depth stop for the anchor construct 40. Once the anchor is inserted to the proper depth, the all-suture anchor 8 is deployed by turning the knob 32 on the inserter. The anchor is pulled upwardly by the floating sutures 34 and expands to compress against the walls of the bone tunnel, securing it within the bone. Once it is fully deployed, the inserter is removed by pulling it axially away from the bone surface. The paddle end 18 of the wick 10 is pulled out of the deployment tube sleeve 14 and can be folded down to sit on the surface of the bone, as shown in FIG. 15. The wick 10 provides a pathway to move bone marrow constituents from the bone tunnel up to the interface between the bone surface (beneath the paddle portion 18) and the soft tissue 36 (above the paddle 18).

Figure 16:
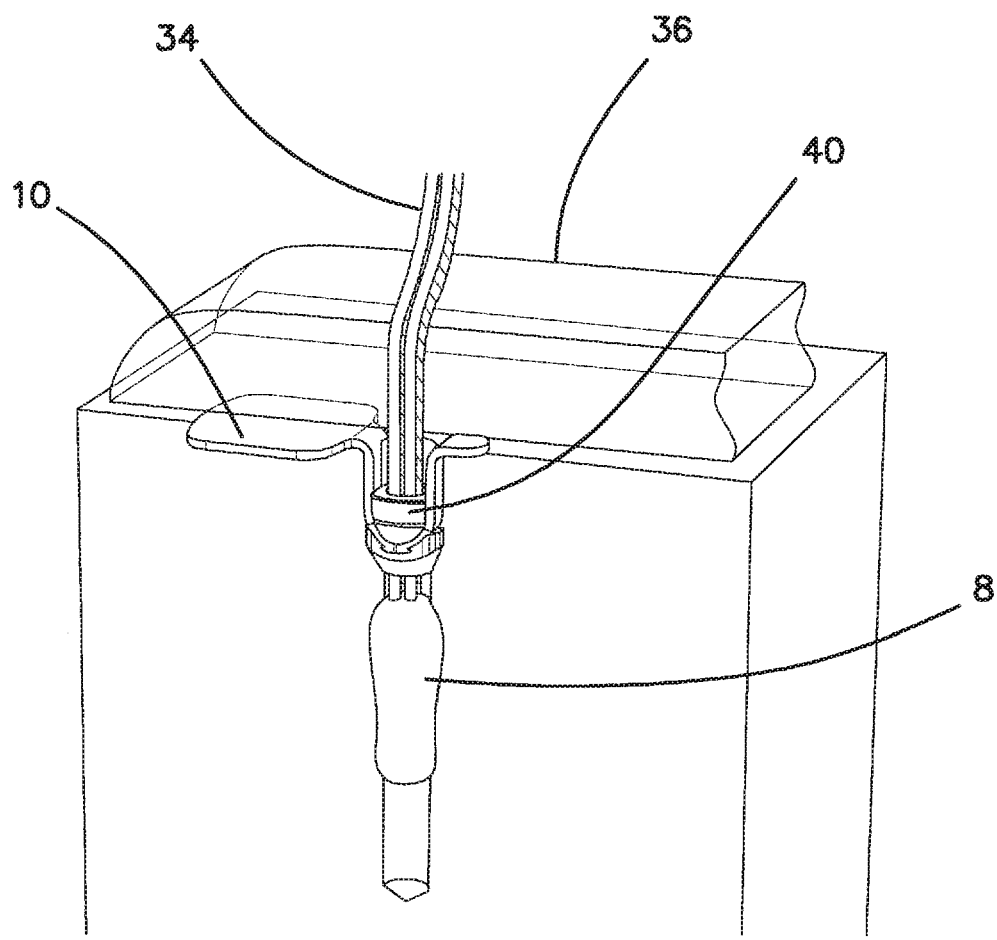
FIG. 16 is an isometric view of the deployed hybrid anchor construction of FIGS. 11-15.

As shown in FIG. 16, the repair is completed by passing the floating sutures 34 through soft tissue 36, and knots are tied to secure the soft tissue against the bone 30, sandwiching the wick material 10 between the bone 30 and tissue 36.

Figure 17:
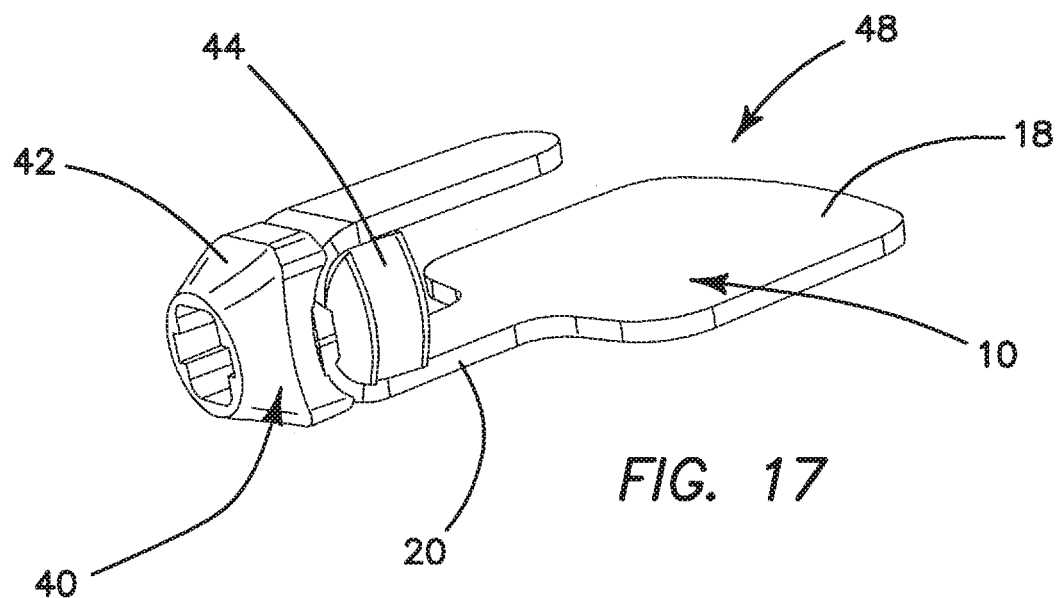
FIG. 17 is an isometric view of an add-on wick assembly constructed in accordance with the principles of the present invention.

A logical extension of the all-suture PEEK hybrid anchor concept disclosed above is a separate system that only comprises the two-part PEEK anchor and wick components, as shown in FIG. 17. This assembly 48 may be loaded into an inserter that allows the practitioner to deploy the assembly on top of any traditional pre-loaded suture anchor, after that anchor has been implanted and deployed. Examples of such anchors, by no means limiting, include the suture anchors sold by the assignee, Cayenne Medical, Inc., under the trademarks QUATTRO X or SURELOCK, but other competitor's pre-loaded suture anchors may be employed as well.

Figure 18:
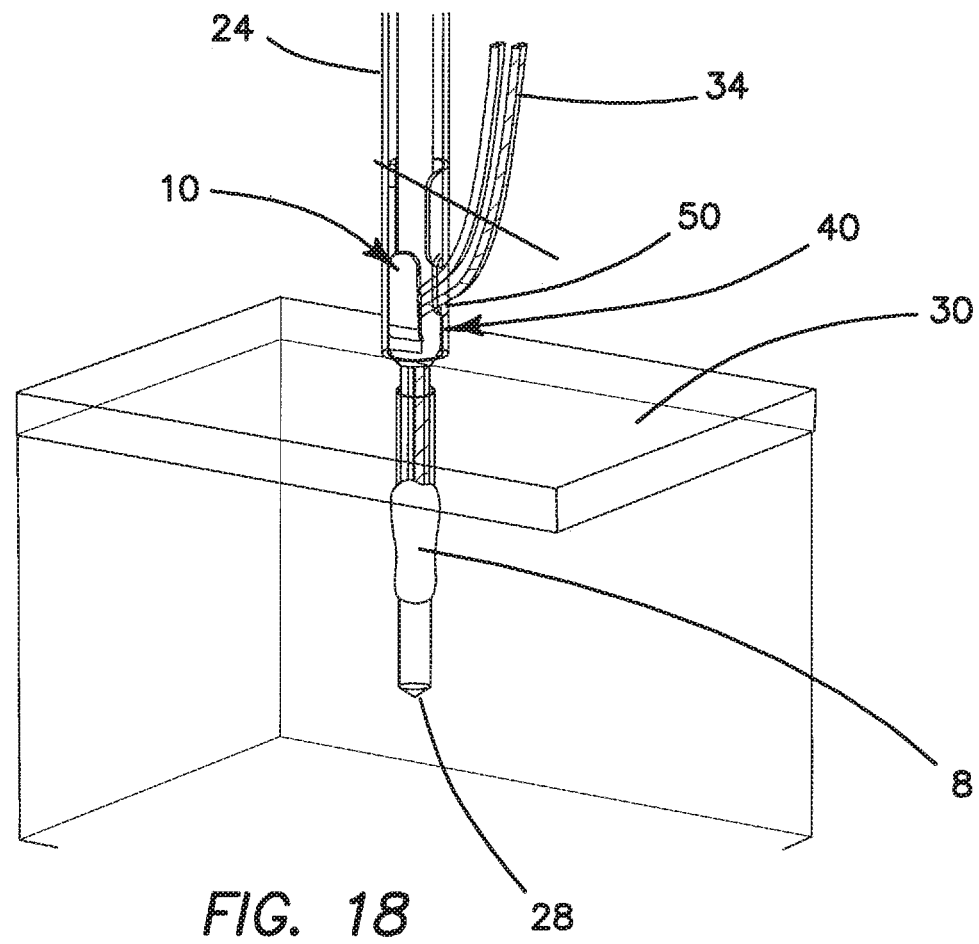
FIG. 18 is an isometric view of the add-on wick assembly of FIG. 17 in a deployed configuration.

Now with reference particularly to FIG. 18, as well as FIG. 17, a procedure for implanting the assembly 48 will be described. This procedure comprises first deploying a pre-loaded suture anchor 8 into the desired procedural site, which may comprise the footprint of the rotator cuff, as discussed in connection with the preceding embodiments, and includes a bone tunnel 28 and a bone surface 30. The pre-loaded suture anchor 8 may include an all-suture suture anchor, or one of the screw-in or push-in type, for example. The floating sutures 34 from the suture anchor are snared through the tip of the inserter, through the center of the anchor wick assembly, and out through a window 50 in the inserter shaft. The inserter tip travels down the floating sutures 34 to the suture anchor 8. The proximal end of the inserter is malleted lightly to drive the two-piece PEEK and wick anchor into the tunnel 28, above the suture anchor. The inserter is removed and the wick 10 is flattened against the bone surface. The floating sutures 34 are passed through the rotator cuff tissue. Knots are tied over the top of the tissue, securing the soft tissue against the bone and sandwiching the wick between the bone and tissue, as in the prior embodiments.

While the foregoing particular embodiments and methods have been shown and described, particularly in connection with the repair of a rotator cuff, one skilled in the art will recognize other suitable applications for the disclosed system and methods. The system is applicable in any situation wherein suture anchors are appropriately used, to assist in promoting the healing process, by the use of a suture anchor with a built-in aligned monophasic nanofiber or microfiber scaffold placed as an interpositional material between a repaired soft tissue member and the underlying bone insertion site, for improvement of the speed of soft tissue healing, strength of the healed soft tissue, cellular patterns at the insertion site; and no requirement for modification to accepted arthroscopic standard-of-care technique. Examples include, but are not limited to, the repair of biceps tenodesis, repair of osteo condral defects, glenoid repair, meniscal repair, tendon repair, or the repair of ACL (anterior cruciate ligament), in conjunction with the usage of the APERFIX® system, manufactured and sold by the assignee, Cayenne Medical, Inc.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. An anchoring system for securing soft tissue to bone, comprising:
    a delivery shaft with a distal end;
    an all-suture anchor received on the distal end of the delivery shaft for arthroscopically delivering the all-suture anchor into a tunnel formed in a bone, the all-suture anchor pullable a distance back through the tunnel following delivery for expanding the all-suture anchor in the tunnel to secure the all-suture anchor in the tunnel; and
    a single unitary piece of fiber material, the single unitary piece of fiber material including a distal portion having a first width permitting the distal portion to be received in the tunnel along with the all-suture anchor, the single unitary piece of fiber material further including a proximal head portion that is to reside outside the tunnel sandwiched between the soft tissue and the bone in the form of a sheet for promoting a healing response between the soft tissue and the bone when the distal portion is received in the tunnel, the proximal head portion having a second width that is wider than said first width, the distal portion having a hole formed therein through which the distal end of the delivery shaft with the all-suture anchor received thereon extends.

2. The anchoring system of claim 1 further comprising a floating suture coupled to the all-suture anchor for extending back out of the tunnel through an opening in an outer surface of the bone when the all-suture anchor is received in the tunnel.

3. The anchoring system of claim 2, wherein floating suture extends through the hole in the distal portion of the single unitary piece of fiber material.

4. The anchoring system of claim 1, wherein the single unitary piece of fiber material provides a pathway for cell travel from bone marrow within the tunnel to an area between the soft tissue and the bone.

5. An anchoring system for securing soft tissue to bone, comprising:
    a single unitary piece of fiber material, the single unitary piece of fiber material including a distal portion having a first width permitting the distal portion to be received in a tunnel formed in a bone, the single unitary piece of fiber material further including a proximal head portion that is to reside outside the tunnel sandwiched between the soft tissue and the bone in the form of a sheet for promoting a healing response between the soft tissue and the bone when the distal portion is received in the tunnel, the proximal head portion having a second width that is wider than said first width, the distal portion having a first hole formed therein;
    a distal anchor element receivable in the tunnel along with the distal portion of the single unitary piece of fiber material, the distal anchor element having a second hole formed therein; and
    a delivery shaft extending through the first hole in the distal portion of the single unitary piece of fiber material and through the second hole in the distal anchor element for delivering the distal portion and the distal anchor element, respectively, into the tunnel, wherein the second hole is positioned distal of the first hole on the delivery shaft such that the distal anchor element is able to provide a shield for portions of the single unitary piece of fiber material as the distal anchor element is being delivered into the tunnel on the delivery shaft.

6. The anchoring system of claim 5 further comprising a suture anchor received on the delivery shaft.

7. The anchoring system of claim 6, wherein a leading end of the suture anchor is positioned distal of the distal anchor element on the delivery shaft.

8. The anchoring system of claim 7, wherein the suture anchor is pre-loaded with a floating suture that can extend back out of the tunnel through an opening in an outer surface of the bone when the suture anchor is received in the tunnel.

9. The anchoring system of claim 8, wherein the floating suture extends through the first hole in the distal portion of the single unitary piece of fiber material and through the second hole in the distal anchor element.

10. The anchoring system of claim 6, wherein the suture anchor is a screw-in anchor.

11. The anchoring system of claim 6, wherein the suture anchor is an all-suture anchor deliverable arthroscopically into the tunnel, the all-suture anchor pullable a distance back through the tunnel following delivery for expanding the all-suture anchor in the tunnel to secure the all-suture anchor in the tunnel.

12. The anchoring system of claim 5, wherein the distal anchor element is anchorable to bone in the tunnel.

13. The anchoring system of claim 12, wherein the distal anchor element is barbed.

14. The anchoring system of claim 5, wherein the single unitary piece of fiber material provides a pathway for cell travel from bone marrow within the tunnel to an area between the soft tissue and the bone.

15. The anchoring system of claim 5 further comprising a proximal anchor element, the proximal anchor element having a third hole formed therein through which the delivery shaft also extends, wherein the first hole in the distal portion of the single unitary piece of fiber material is positioned between the second hole in the distal anchor element and the third hold in the proximal anchor element on the delivery shaft.

16. An anchoring system for securing soft tissue to bone, comprising:
a suture that is anchorable in a tunnel formed in a bone for extending back out of the tunnel through an opening in an outer surface of the bone in an anchored fashion;
a single unitary piece of fiber material, the single unitary piece of fiber material including a distal portion having a first width permitting the distal portion to be received in a tunnel formed in a bone, the single unitary piece of fiber material further including a proximal head portion that is to reside outside the tunnel sandwiched between the soft tissue and the bone in the form of a sheet for promoting a healing response between the soft tissue and the bone when the distal portion is received in the tunnel, the proximal head portion having a second width that is wider than said first width, the distal portion having a first hole formed therein through which the suture extends to couple the single unitary piece of fiber material to the suture; and
a distal anchor element receivable in the tunnel along with the distal portion of the single unitary piece of fiber material, the distal anchor element having a second hole formed therein through which the suture extends to couple the distal anchor element to the suture.

17. The anchoring system of claim 16 further comprising a suture anchor coupled to the suture, wherein a leading end of the suture anchor is positioned distal of the distal anchor element such that the second hole in the distal anchor element is positioned between the leading end of the suture anchor and the first hole in the distal portion of the single unitary piece of fiber material along the suture.

18. The anchoring system of claim 17, wherein the suture anchor is an all-suture anchor deliverable arthroscopically into the tunnel, the all-suture anchor pullable a distance back through the tunnel following delivery for expanding the all-suture anchor in the tunnel to secure the all-suture anchor in the tunnel.

19. The anchoring system of claim 16 further comprising a proximal anchor element, the proximal anchor element having a third hole formed therein through which the suture extends to couple the proximal anchor element to the suture, wherein the first hole in the distal portion of the single unitary piece of fiber material is positioned between the second hole in the distal anchor element and the third hold in the proximal anchor element along the suture.

20. The anchoring system of claim 19, wherein the distal anchor element and the proximal anchor element are anchorable to bone in the tunnel.

* * * * *